US00PP09945P

United States Patent [19]

Rabin

[11] Patent Number: Plant 9,945

[45] Date of Patent: Jul. 1, 1997

[54] GUZMANIA PLANT NAMED 'PURPLE KNIGHT'

[75] Inventor: Mitch Rabin, Goulds, Fla.

[73] Assignee: Twyford International, Inc., Santa Paula, Calif.

[21] Appl. No.: 597,031

[22] Filed: Feb. 5, 1996

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Guzmania plant named 'Purple Knight' having large, wide, compact, clean, long-lasting, red-purple inflorescence with white tipped terminal bracts.

2 Drawing Sheets

The present invention relates to a new and distinct cultivar of Guzmania, a genus within the family bromeliaceae, hereinafter referred to by the cultivar name 'Purple Knight'. The new cultivar is an unusual selection discovered among a group of plants of F1 hybrid Guzmania 'Ruby' grown from seeds.

Guzmania comprise a genus of more 100 species of evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight, and during the spring to autumn period, the central vase-like part of the leaf rosette is normally filled with water.

Guzmania is native to tropical America. Leaves of Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots produced by the plant which may then be rooted. The resulting off-shoots are detached from the mother plant and may be grown in an appropriate soil or bark mixture. Many types are propagated relatively uniformly from seeds.

The new cultivar 'Purple Knight' was discovered by the inventor Mitch Rabin in Goulds, Fla. growing among plants of seed derived F1 hybrid Guzmania 'Ruby'. The selection comprising the new variety was chosen after commencement of flowering in June 1989. The new cultivar was recognized for its unusual inflorescence. Subsequent asexual propagation by off-shoots by the inventor in Goulds, Fla. has demonstrated that the combination of characteristics as herein disclosed for the new cultivar 'Purple Knight' are firmly fixed and are retained through successive generations of asexual reproduction.

The following traits have been repeatedly observed to be characteristics which in combination distinguish 'Purple Knight' from the unpatented parent 'Ruby' to which reference is made. 'Ruby' is known for its tall, dark red-purple, long lasting inflorescence, and dark green glossy foliage.

1. The inflorescence produced by 'Purple Knight' is much broader and shorter than that of 'Ruby'.

2. 'Purple Knight' has wide, dark red-purple bracts with contrasting white tipped terminal bracts.

3. Vestigial and functional flowers are present in the terminal part of the spike, and in lateral branch spikes. The flowers however, emerge from under the bracts.

4. Because the flowers are few, and only partially emerge from under the bracts, the inflorescence is cleaner appearing and longer lasting. The inflorescence does not appear "flowered-out" with age.

'Purple Knight' has not been tested under all available environmental conditions. The phenotype may vary with variations in environmental conditions such as temperature, light intensity, daylength and humidity without, however, any variance in genotype.

The accompanying color photographic drawings show typical characteristics of 'Purple Knight', with colors being as true as possible with illustrations of this type.

The photograph on sheet 1 is of a 12-month-old plant of 'Purple Knight' grown from an off-shoot, and finished in a 15.5 cm pot.

The photograph on sheet 2 shows in more detail the inflorescence of 'Purple Knight'.

The following description is based on the plant illustrated on sheets 1 and 2. The plant was grown in Goulds, Fla. by the inventor in shadehouse conditions which are typical of the industry. Color references are made to The Royal Horticultural Society Colour Chart (R.H.S.).

I. Plant:

*Form/growth habit.*—Basal Rosette of strap-like leaves arranged around a central axis.

*Height.*—Approximately 43 cm including inflorescence.

*Diameter.*—Approximately 75–80 cm.

II. Foliage:

*Size of leaf.*—The basal leaves are approximately 45.5–48 cm long, and 3.7–4.2 cm wide.

*Shape of leaf.*—The leaf blade is ligulate with an acute apiculate tip. The surface is flat or slightly channeled. The margins are entire.

*Surface texture.*—The leaf blade is thin, coriaceous, smooth and glossy.

*Color.*—The leaves are medium green throughout the foliage. The adaxial surface is darker and greener than but closest to 137 A, and the abaxial surface is greener than but closest to 147 B. The innermost leaf surfaces are flushed or striated with red-purple 59 A.

*Average number of leaves.*—The plant produces approximately 20–24 leaves before producing an inflorescence.

*Roots.*—Roots are white changing to brown, and wiry with fine laterals.

III. Bracts:

*Size and color.*—The uppermost terminal bracts are approximately 5.5–7.5 cm long and 1.5–2.3 cm wide, and are red-purple 59 A in color, with the most apical tipped with white.

The primary bracts are approximately 16–19 cm long, diminishing to 10–14 cm long near the terminal, and 3.5–3.7 cm wide, diminishing to 2.7–3.0 cm wide near the terminal. The adaxial and abaxial surfaces are dark red-purple 59 A in color. The tips of the primary bracts are dark anthocyanous 187 A in color.

The scape bracts are approximately 25–30 cm long, and approximately 3.9–4.2 cm wide. The adaxial surface color is 137 A. The abaxial surface is greener than but closest to 147 B, with red-purple 59 A areas where the bract separates from the stem.

*General shape.*—The bracts are ligulate with acute tips, densely imbricate in vertical ranks along the capitate inflorescence.

*Number.*—Terminal bracts, approximately 10. Primary bracts, approximately 10–15. Scape bracts, approximately 7.

*Texture.*—Smooth and glossy.

*Margin.*—Entire.

*Scape.*—The scape is approximately 35 cm tall, approximately 9–12 mm in diameter, and 145 B in color.

IV. Flowers:

*Borne.*—One to three, short, 3–6 cm long; vestigial lateral branches are concealed under bracts, or terminal in the inflorescence.

*Shape of inflorescence.*—The inflorescence is star-shaped when viewed from above, terminal in origin, and densely pennate.

*Individual flowers.*—Approximately 30 flower buds present, terminal in the inflorescence and concealed under bracts. Calyx: Gamosepalous, three sepals present, each 3.6 cm long, 0.6 cm wide, and translucent 11 D in color. Corolla: Gamopetalous, three petals present, each 2.7 cm long, 0.5 cm wide, and yellow 8 B in color.

*Time of blooming.*—In mature plants, the inflorescence is in full color approximately 14 weeks after induction, at any time of the year.

*Duration of inflorescence.*—The inflorescence will hold its color approximately 3–6 months.

V. Reproductive organs:

*Ovary.*—Superior, three locules, 9 mm long, 2.5 mm wide, 150 D in color.

*Style.*—16 mm long, 0.8 mm wide, 150 D in color.

*Stamens.*—Six present; filament 14 mm long; anthers 8 mm long, yellow 11 D in color.

VI. Seed characteristics: Sterile F1 hybrid.

It is claimed:

1. A new and distinct cultivar of Guzmania plant named 'Purple Knight', as illustrated and described.

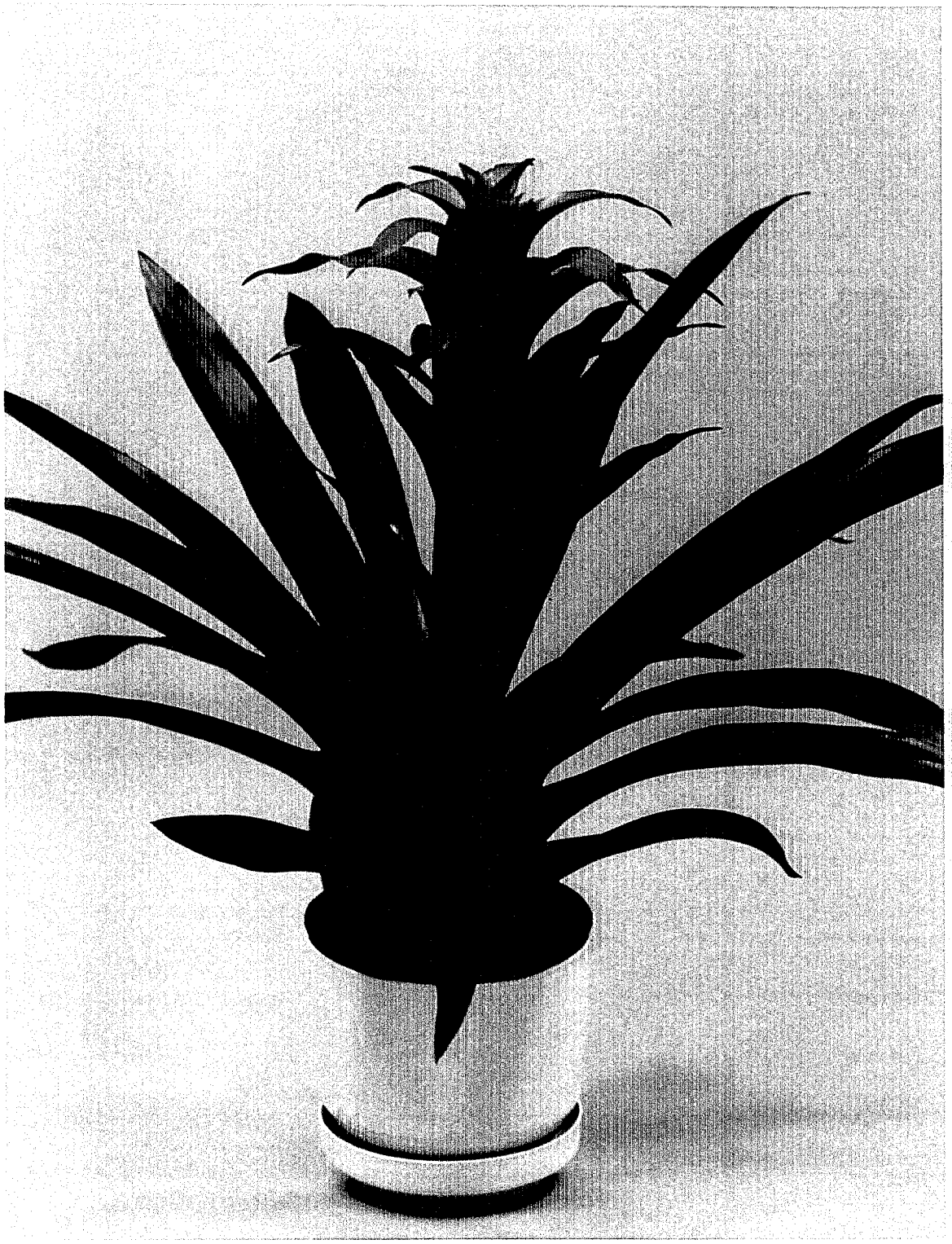

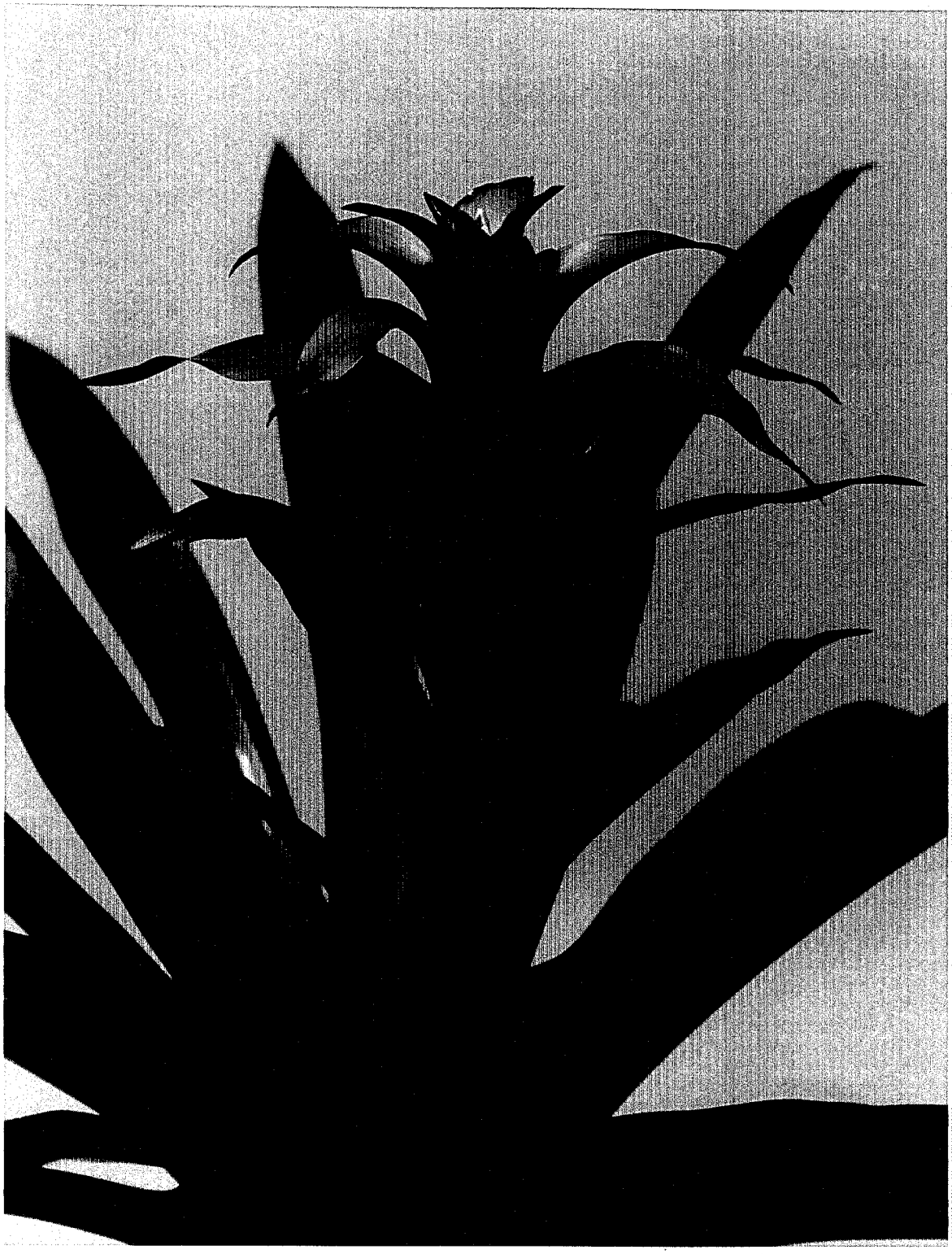

* * * * *